US012693162B2

(12) United States Patent
Shi et al.

(10) Patent No.: US 12,693,162 B2
(45) Date of Patent: Jul. 28, 2026

(54) OFFSET VOLTAGE COMPENSATION CIRCUIT AND ISOLATION AMPLIFIER DEVICE INCLUDING THE SAME

(71) Applicant: LITE-ON SINGAPORE PTE. LTD., Singapore (SG)

(72) Inventors: Wei Shi, Singapore (SG); Darmayuda Imade, Singapore (SG)

(73) Assignee: LITE-ON SINGAPORE PTE. LTD., Singapore (SG)

(*) Notice: Subject to any disclaimer, the term of this patent is extended or adjusted under 35 U.S.C. 154(b) by 437 days.

(21) Appl. No.: 18/527,342

(22) Filed: Dec. 3, 2023

(65) Prior Publication Data

US 2024/0223143 A1 Jul. 4, 2024

(30) Foreign Application Priority Data

Dec. 30, 2022 (SG) ............................ 10202260647U

(51) Int. Cl.
H03F 1/02 (2006.01)
G01J 3/36 (2006.01)
(Continued)

(52) U.S. Cl.
CPC ........... G01J 3/36 (2013.01); G01N 33/4833 (2013.01); G01S 17/04 (2020.01); G02B 1/002 (2013.01);
(Continued)

(58) Field of Classification Search
CPC ..... G01J 3/36; G01J 2003/2806; G01S 17/04; G01N 33/4833; G01N 2021/3568;
(Continued)

(56) References Cited

U.S. PATENT DOCUMENTS 6,952,130 B2 * 10/2005 Kuyel ................. H03F 3/45986
330/289
7,209,001 B2 * 4/2007 Ha ............................ H03F 3/08
330/254
(Continued)

FOREIGN PATENT DOCUMENTS

WO WO-2019097870 A1 * 5/2019 ............... H03F 3/45

OTHER PUBLICATIONS

AN-105Fa, Application Note of Linear Technologies, Dec. 2005 (Year: 2005).*
(Continued)

*Primary Examiner* — Hafizur Rahman
(74) *Attorney, Agent, or Firm* — Li & Cai Intellectual Property Office

(57) ABSTRACT

An offset voltage compensation circuit and an isolation amplifier device including the same are provided. The offset voltage compensation circuit includes a first amplifier, a second amplifier, a first current source, a second current source, a first resistor and a second resistor. The first amplifier has a first input connected to a first differential input node and a first output connected to a first differential output node. The second amplifier has a first input connected to a second differential input node and a second output connected to a second differential output node. The first current source is connected to the first amplifier for providing a first current. The second current source is connected to the second amplifier for providing a second current. The first current source is controlled according to the second current and a difference between a first initial output voltage and a second initial output voltage.

20 Claims, 5 Drawing Sheets

(51) Int. Cl.

| | |
|---|---|
| *G01N 33/483* | (2006.01) |
| *G01S 17/04* | (2020.01) |
| *G02B 1/00* | (2006.01) |
| *G02B 5/20* | (2006.01) |
| *G02B 5/28* | (2006.01) |
| *G02B 26/00* | (2006.01) |
| *H03F 1/22* | (2006.01) |
| *H03F 3/45* | (2006.01) |
| *H03F 3/68* | (2006.01) |
| *G01J 3/28* | (2006.01) |
| *G01N 21/3563* | (2014.01) |

(52) U.S. Cl.

CPC ............. *G02B 5/201* (2013.01); *G02B 5/286* (2013.01); *G02B 26/001* (2013.01); *H03F 1/223* (2013.01); *H03F 3/45237* (2013.01); *H03F 3/45475* (2013.01); *H03F 3/45748* (2013.01); *H03F 3/68* (2013.01); *G01J 2003/2806* (2013.01); *G01N 2021/3568* (2013.01); *G01N 2201/125* (2013.01); *G02B 2207/101* (2013.01); *H03F 2200/165* (2013.01); *H03F 2200/375* (2013.01); *H03F 2203/45151* (2013.01); *H03F 2203/45212* (2013.01)

(58) Field of Classification Search

CPC .. G01N 2201/125; G02B 1/002; G02B 5/201; G02B 5/286; G02B 26/001; G02B 2207/101; H03F 1/223; H03F 3/45237; H03F 3/45475; H03F 3/45748; H03F 3/68; H03F 2200/165; H03F 2203/45151; H03F 2203/45212

USPC ........................................................ 330/260

See application file for complete search history.

(56) References Cited

U.S. PATENT DOCUMENTS

| | | | | |
|---|---|---|---|---|
| 2004/0184387 | A1* | 9/2004 | Shirasaka ............ | G11B 7/1275 369/124.1 |
| 2019/0327002 | A1* | 10/2019 | Foong .................. | H04B 10/695 |
| 2019/0363686 | A1* | 11/2019 | Grasso ............... | H03F 3/45188 |
| 2023/0032759 | A1* | 2/2023 | Haseeb .............. | H03F 3/45183 |

OTHER PUBLICATIONS

Application Note and Tutorial of Analog Devices, MT-076 (Year: 2009).*

Learn About Three-Op Amp Instrumentation Amplifiers, Technical Article Mar. 29, 2021 by Dr. Steve Arar (Year: 2021).*

* cited by examiner

100

OFFSET VOLTAGE COMPENSATION CIRCUIT AND ISOLATION AMPLIFIER DEVICE INCLUDING THE SAME

CROSS-REFERENCE TO RELATED PATENT APPLICATION

This application claims the benefit of priority to Singapore Provisional Patent Application Ser. No. 10202260647U, filed on Dec. 30, 2022, which application is incorporated herein by reference in its entirety.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a circuit and a device, and more particularly to an offset voltage compensation circuit and an isolation amplifier device including the same.

BACKGROUND OF THE DISCLOSURE

In the related art, isolation amplifiers are a type of isolation device designed for current and voltage sensing in applications including motor drives and renewable energy systems.

In a typical motor drive implementation, after a current flows through an external resistor, a resulting voltage drop is sensed by the isolation amplifier. A differential pair of output signals that is proportional to the current is created on another side of an isolation barrier of the isolation amplifier.

An offset voltage within the differential pair of output signals may affect the performance of the isolation amplifier, and should be compensated by carefully design IC circuit, layout or package. However, certain systematic offset may still present in the isolation amplifier that is carefully designed. A compensation method will be useful to address such unexpected systematic offset voltage.

SUMMARY OF THE DISCLOSURE

In response to the above-referenced technical inadequacies, the present disclosure provides an offset voltage compensation circuit and an isolation amplifier device including the same.

In order to solve the above-mentioned problems, one of the technical aspects adopted by the present disclosure is to provide an offset voltage compensation circuit, which includes a first amplifier, a second amplifier, a first current source, a second current source, a first resistor and a second resistor. The first amplifier has a first input connected to a first differential input node and a first output connected to a first differential output node. The second amplifier has a first input connected to a second differential input node and a second output connected to a second differential output node. The first current source is connected to a second input of the first amplifier for providing a first current. The second current source is connected to a second input of the second amplifier and configured to provide a second current. The first resistor is connected between the second input of the first amplifier and the first output. The second resistor is connected between the second input of the second amplifier and the second output. The first current source is controlled according to the second current and a difference between a first initial output voltage and a second initial output voltage, such that an offset voltage between the first output and the second output is compensated.

Therefore, in the offset voltage compensation circuit and the isolation amplifier device including the same provided by the present disclosure, the compensation circuit arranged in the last output stage can compensate the output offset voltage, so as to achieve relaxation of accuracy requirement.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
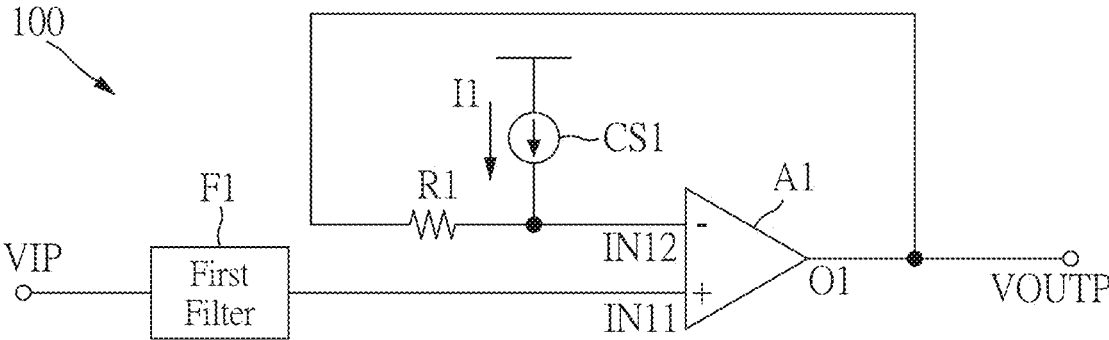
FIG. 1 is a schematic circuit of an offset voltage compensation circuit according to a first embodiment of the present disclosure.
Figure 1:
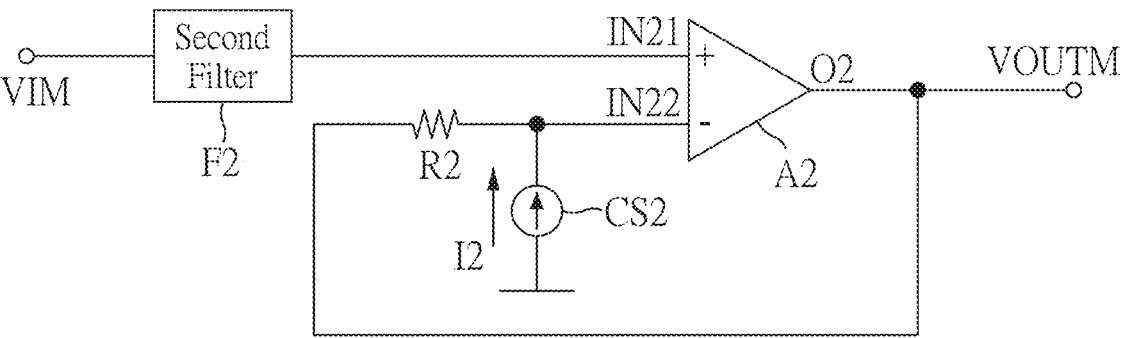

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a," "an" and "the" includes plural reference, and the meaning of "in" includes "in" and "on." Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first," "second" or "third" can be used to describe various components, signals or the like, which are for distinguishing one component/signal from another one only, and are not intended to, nor should be construed to impose any substantive limitations on the components, signals or the like.

First Embodiment

FIG. 1 is a schematic circuit of an offset voltage compensation circuit according to a first embodiment of the present disclosure.

Referring to FIG. 1, a first embodiment of the present disclosure provides an offset voltage compensation circuit 100, which includes a first amplifier A1, a second amplifier A2, a first current source CS1, a second current source CS2, a first resistor R1 and a second resistor R2.

Specifically, the offset voltage compensation circuit 100 of FIG. 1 is designed for non-inverting amplifiers, that is, the first amplifier A1 is a non-inverting amplifier. The first amplifier A1 has multiple terminals that includes a positive input IN11, a negative input IN12, and a first output O1. The positive input IN11 is connected to a first differential input node VIP, and the first output O1 is connected to a differential output node VOUTP.

Similarly, the second amplifier A2 is also a non-inverting amplifier, which has multiple terminals that includes a positive input IN21, a negative input IN22 and a second output O2.

The positive input IN21 is connected to a second differential input node VIM, and the second output O2 is connected to a differential output node VOUTM. The first amplifier A1 and the second amplifier A2 are used to amplify a differential pair of input signals.

The first current source CS1 is connected to the negative input IN12 for providing a first current I1. The second current source CS2 is connected to the negative input IN22 for providing a second current I2.

The first resistor R1 is connected between the negative input IN12 and the first output O1, that is, the first resistor R1 is arranged on a negative feedback path of the first amplifier A1. The second resistor R2 is connected between the negative input IN22 and the second output O2, that is, the second resistor R2 is arranged on a negative feedback path of the second amplifier A2. It should be noted that the first current source CS1, the second current source CS2, the first resistor R1 and the second resistor R2 are designed for achieving offset compensation, and details thereof will be illustrated hereinafter.

In this embodiment, filters such as low pass filters or high pass filters can be provided for filtering out certain frequency components according to requirements. For example, the offset voltage compensation circuit 100 of FIG. 1 further includes a first filter F1 and a second filter F2. The first filter F1 is connected between the first differential input node VIP and the positive input IN11, and the second filter F2 is connected between the second differential input node VIM and the positive input IN21. The first filter F1 and the second filter F2 can be low pass filters, such as passive resistor-capacitor filters. For example, the low pass filter only allows low frequency signals with frequencies from 0 Hz to a cut-off frequency point fc of the low pass filter to pass, such as 100 kHz, while blocking those any higher. However, the aforementioned details are disclosed for exemplary purposes only, and are not meant to limit the scope of the present disclosure.

It should be noted that the differential pair of input signals with the same voltages are provided through the first differential input node VIP and the second differential input node VIM. Assuming that a first initial output voltage of the differential output node VOUTP and a second initial output voltage of the differential output node VOUTM without offset compensation (i.e., R1=0, I1=I2=0) are Vop and Vom, respectively, an output offset voltage can therefore be obtained according to the following equation (1):

$$Voos = Vop - Vom; \qquad\qquad \text{equation(1)}$$

where Voos represents the output offset voltage, Vop represent the first initial output voltage, and Vom represents the second initial output voltage.

After components designed for offset compensation (i.e., the first current source CS1, the second current source CS2, the first resistor R1 and the second resistor R2) are added, a first output voltage of the differential output node VOUTP and a second output voltage of the differential output node VOUTM after offset compensation can be obtained according to the following equations (2) and (3):

$$Vop' = Vop - I1^*R1; \qquad\qquad \text{Equation (2)}$$

$$Vom' = Vom - I2^*R2; \qquad\qquad \text{Equation (3)}$$

where Vop' represents the first output voltage of the differential output node VOUTP after offset compensation, Vom' represents the second output voltage of the differential output node VOUTM after offset compensation, I1 represents the current provided by the first current source CS1, I2 is the current provided by the second current source CS2, R1 represents a resistance of the first resistor R1, and R2 represents a resistance of the second resistor R2.

Assuming that resistances of the first resistor R1 and the second resistor R2 are both R0, an output offset voltage after offset compensation can be obtained according to the following equation (4):

$$Voos' = Vop' - Vom' = \qquad\qquad \text{Equation (4)}$$
$$(Vop - Vom) - (I1 - I2)^*R0 = Voos - (I1 - I2)^*R0;$$

where Voos' represents the output offset voltage after offset compensation.

As can be seen from equation (4), if the currents I1 and I2 and the resistances of the first resistor R1 and the second resistor R2 are carefully designed, the output offset voltage Voos' can be eliminated.

In some embodiments, one of the first current source CS1 and the second current source CS2 can be an adjustable current source, and the other of the first current source CS1 and the second current source CS2 can be a constant current source. Taking the first current source CS1 being the adjustable current source as an example, if the current I1 provided by the first current source CS1 is controlled to a specific value, the output offset voltage can be compensated to 0. For example, the current I1 provided by the first current source CS1 can be controlled according to the following equation (5):

$$I1 = I2 + Voos / R0. \qquad \text{Equation (5)}$$

That is, after the first current source CS1 is controlled according to the current I2 provided by the second current source CS2 and a difference between a first initial output voltage and a second initial output voltage (i.e., the output offset voltage Voos before offset compensation), an offset voltage between the first output O1 and the second output O2 can be compensated, that is, the difference between the voltages of the first output O1 and the second output O2 is approximated to 0. In addition, the current I1 is controlled to be larger or smaller than the current I2 to compensate the offset voltage between the first output O1 and the second output O2. In certain embodiments, the current I1 can be controlled to a current value that is inversely proportional to the resistance R0, so as to compensate the offset voltage between the first output O1 and the second output O2.

In other embodiments, if the second current source CS2 is the adjustable current source while the first current source CS1 being the constant current source, the current I2 provided by the second current source CS2 can be similarly controlled according to equation (5) modified by exchanging I1 with I2.

In certain embodiments, the first resistor R1 and the second resistor R2 can be adjustable resistors and can be controlled according to equation (5) for the purpose of achieving offset compensation.

Furthermore, a controller can be provided in the offset voltage compensation circuit 100 to adjust any controllable components such as the adjustable current source(s) and adjustable resistor(s).

However, the aforementioned description for the offset voltage compensation circuit 100 of the first embodiment is merely an example, and is not meant to limit the scope of the present disclosure.

It should be noted that the offset voltage consists of a random offset voltage and a systematical offset voltage. The random offset voltage mainly stems from random variation of integrated circuit (IC) or package process, which is difficult to compensate and should be reduced by optimizing process or increasing device size. The systematical offset voltage comes from certain improper IC circuit, layout or package design, and can be compensated by carefully design for all devices.

For certain systematic offset that still present in the isolation amplifier, by arranging the compensation circuit provided by the present disclosure in the last output stage, such systematic offset can be compensated to achieve relaxation of accuracy requirement.

Second Embodiment

Figure 2:
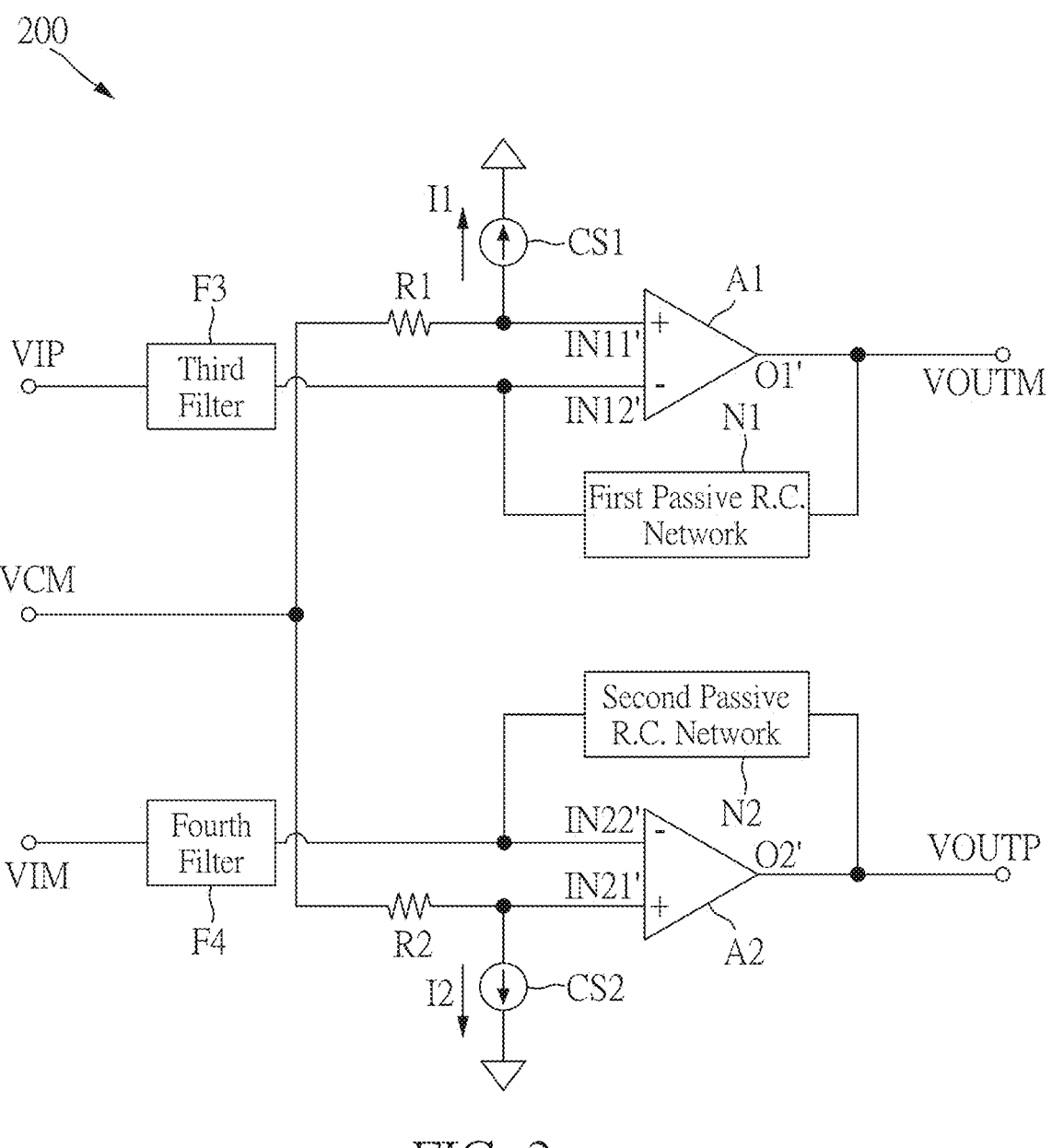
FIG. 2 is a schematic circuit layout of an offset voltage compensation circuit according to a second embodiment of the present disclosure.

FIG. 2 is a schematic circuit layout of an offset voltage compensation circuit according to a second embodiment of the present disclosure.

Referring to FIG. 2, a second embodiment of the present disclosure provides an offset voltage compensation circuit 200, which includes a first amplifier A1, a second amplifier A2, a first current source CS1, a second current source CS2, a first resistor R1 and a second resistor R2.

The first amplifier A1 has multiple terminals that includes a positive input IN11', a negative input IN12' and a first output O1'. Specifically, the offset voltage compensation circuit 200 of FIG. 2 is designed for inverting amplifiers, that is, the first amplifier A1 and the second amplifier A2 are inverting amplifiers, therefore, the negative input IN12' is connected to a first differential input node VIP, and the first output O1' is connected to a differential output node VOUTM, which is different from the first embodiment since the first amplifier A1 is the inverting amplifier.

Similarly, the second amplifier A2 has multiple terminals that includes a positive input IN21', a negative input IN22' and a second output O2', and the second amplifier A2 is also the inverting amplifier. The negative input IN22' is connected to a second differential input node VIM, and the second output O2' is connected to a differential output node VOUTP. The first amplifier A1 and the second amplifier A2 are used to amplify and invert a differential pair of input signals.

The first current source CS1 is connected to the positive input IN11' for providing a first current I1. The second current source CS2 is connected to the positive input IN21' for providing a second current I2.

The first resistor R1 is connected between a common-mode voltage node VCM and the positive input IN11', and the second resistor R2 is connected between the common-mode voltage node VCM and the positive input IN21'. It should be noted that the first current source CS1, the second current source CS2, the first resistor R1 and the second resistor R2 are designed for achieving offset compensation, and details thereof will be illustrated hereinafter.

In this embodiment, filters such as low pass filters or high pass filters can be provided for filtering out certain frequency components according to requirements. For example, the offset voltage compensation circuit 200 of FIG. 2 further includes a third filter F3 and a fourth filter F4. The third filter F3 is connected between the first differential input node VIP and the negative input IN12', and the fourth filter F4 is connected between the second differential input node VIM and the negative input IN22'. The first filter F1 and the second filter F2 can be low pass filters, such as passive resistor-capacitor filters. However, the aforementioned details are disclosed for exemplary purposes only, and are not meant to limit the scope of the present disclosure.

Furthermore, the offset voltage compensation circuit 200 of FIG. 2 further includes a first passive resistor-capacitor network N1 and a second passive resistor-capacitor network N2. The first passive resistor-capacitor network N1 is connected between the negative input IN12' and the first output O1', that is, the first passive resistor-capacitor network N1 is arranged on a negative feedback path of the first amplifier A1. Similarly, the second passive resistor-capacitor network N2 is connected between the negative input IN22' and the second output O2' and is arranged on a negative feedback path of the second amplifier A2. The first passive resistor-capacitor network N1 and the second passive resistor-capacitor network N2 can be used to stabilize gains and decrease noise of the corresponding amplifiers and result in a more accurate and stable output signals.

It should be noted that the differential pair of input signals with the same voltages are provided through the first differential input node VIP, the second differential input node VIM, and the common-mode voltage node VCM. Assuming that a direct current (DC) gain from an input to an output (e.g., from VIP to O1') is −G0, and a first initial output voltage of the differential output node VOUTP and a second initial output voltage of the differential output node VOUTM without offset compensation (i.e., R1=0, I1=I2=0) are Vop and Vom, respectively, an output offset voltage can therefore be obtained according to the following equation (6):

$$Voos = Vop - Vom; \qquad \text{equation(6)}$$

where Voos represents the output offset voltage before offset compensation, Vop represent the first initial output voltage, and Vom represents the second initial output voltage.

After components designed for offset compensation (i.e., the first current source CS1, the second current source CS2, the first resistor R1 and the second resistor R2) are added, a first output voltage of the differential output node VOUTP and a second output voltage of the differential output node VOUTM after offset compensation can be obtained according to the following equations (7) and (8):

$$Vop' = Vop - I1^{*}R1^{*}(1 + G0); \qquad \text{Equation (7)}$$

$$Vom' = Vom - I2^{*}R2^{*}(1 + G0); \qquad \text{Equation (8)}$$

where Vop' represents the first output voltage of the differential output node VOUTP after offset compensation, Vop' represent the second output voltage of the differential output node VOUTM after offset compensation, I1 represents the current provided by the first current source CS1, I2 is the current provided by the second current source CS2, R1 represents a resistance of the first resistor R1, R2 represents a resistance of the second resistor R2, and G0 represent the gains of the first amplifier A1 and the second amplifier A2.

Assuming that resistances of the first resistor R1 and the second resistor R2 are both R0, an output offset voltage after offset compensation can be obtained according to the following equation (9):

$$Voos' = \qquad \text{Equation (9)}$$
$$Vop' - Vom' = (Vop - Vom) - (1 + G0)^{*}(I1 - I2)^{*}R0 =$$
$$Voos - (1 + G0)^{*}(I1 - I2)^{*}R0;$$

where Voos' represents the output offset voltage after offset compensation.

As can be seen from equation (9), if the currents I1 and I2 and the resistances of the first resistor R1 and the second resistor R2 are carefully designed, the output offset voltage Voos' can be eliminated.

In some embodiments, one of the first current source CS1 and the second current source CS2 can be an adjustable current source, and the other of the first current source CS1 and the second current source CS2 can be a constant current source. Taking the first current source CS1 being the adjustable current source as an example, if the current I1 provided by the first current source CS1 is controlled to a specific value, the output offset voltage can be compensated to 0. For example, the current I1 provided by the first current source CS1 can be controlled according to the following equation (10):

$$I1 = I2 + Voos/(R0^{*}(1 + G0)). \qquad \text{Equation (10)}$$

That is, after the first current source CS1 is controlled according to the current I2 provided by the second current source CS2 and a difference between a first initial output voltage and a second initial output voltage (i.e., the output offset voltage Voos before offset compensation), and the gains of the first amplifier A1 and the second amplifier A2, an offset voltage between the first output O1' and the second output O2' can be compensated, that is, the difference between the voltages of the first output O1' and the second output O2' is approximated to 0.

In other embodiments, if the second current source CS2 is the adjustable current source while the first current source CS1 being the constant current source, the current I2 provided by the second current source CS2 can be similarly controlled according to equation (10) modified by exchanging I1 with I2.

Furthermore, a controller can be provided in the offset voltage compensation circuit 200 to adjust any controllable components such as the above mentioned adjustable current source(s) and adjustable resistor(s).

In certain embodiments, the first resistor R1 and the second resistor R2 can be adjustable resistors and can be controlled according to equation (10) for the purpose of achieving offset compensation.

In certain embodiments, two unity gain buffers such as inverting amplifiers are implemented with; and only one type of current source is used in the compensation circuit 200, thus positive and negative offset compensation can be achieved by the difference of the two amplifiers.

However, the aforementioned description for the offset voltage compensation circuit 200 of the first embodiment is merely an example, and is not meant to limit the scope of the present disclosure.

Third Embodiment

Figure 3:
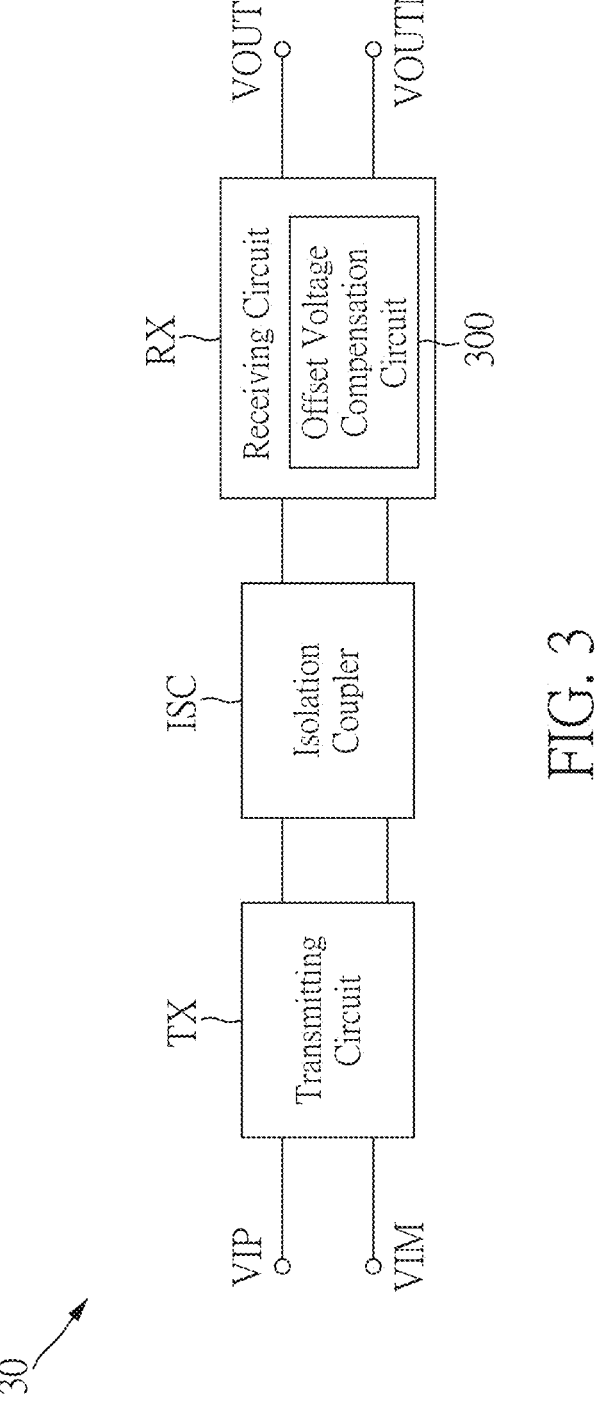
FIG. 3 is a block diagram of an isolation amplifier device according to a third embodiment of the present disclosure.

FIG. 3 is a block diagram of an isolation amplifier device according to a third embodiment of the present disclosure.

Referring to FIG. 3, the third embodiment of the present disclosure provides an isolation amplifier device 30, which includes a transmitting circuit TX, an isolation coupler ISC and a receiving circuit RX.

The transmitting circuit TX can include an input amplifier and a modulator, such as with a 1-bit sigma-delta modulator (SDM) circuit, which is configured to convert a differential pair of input voltages from differential input nodes VIP and VIM to a modulated pulse signal, and the modulated pulse signal can then be used to drive the isolation coupler ISC.

The isolation coupler ISC is also referred to as an isolation barrier, can be configured to be driven by the modulated pulse signal and generate an isolation signal. For example, the isolation coupler ISC can be an optical coupler, a capacitive coupler or an inductive coupler.

The receiving circuit RX can include a demodulator, a filter and an output amplifier, and can be configured to receive, demodulate, filter out certain frequency components and amplify the isolation signal, so as to generate a differential pair of output voltages through differential output nodes VOUTP and VOUTM.

For the isolation amplifier device 30, the last output stage can be a differential non-inverting or inverting amplifier stage, and therefore the amplifier of the receiving circuit RX can include an offset voltage compensation circuit 300 at the output stage, and the offset voltage compensation circuit 300 can be the same as the offset voltage compensation circuit 100 or 200 mentioned in the previous embodiments.

Figure 4:
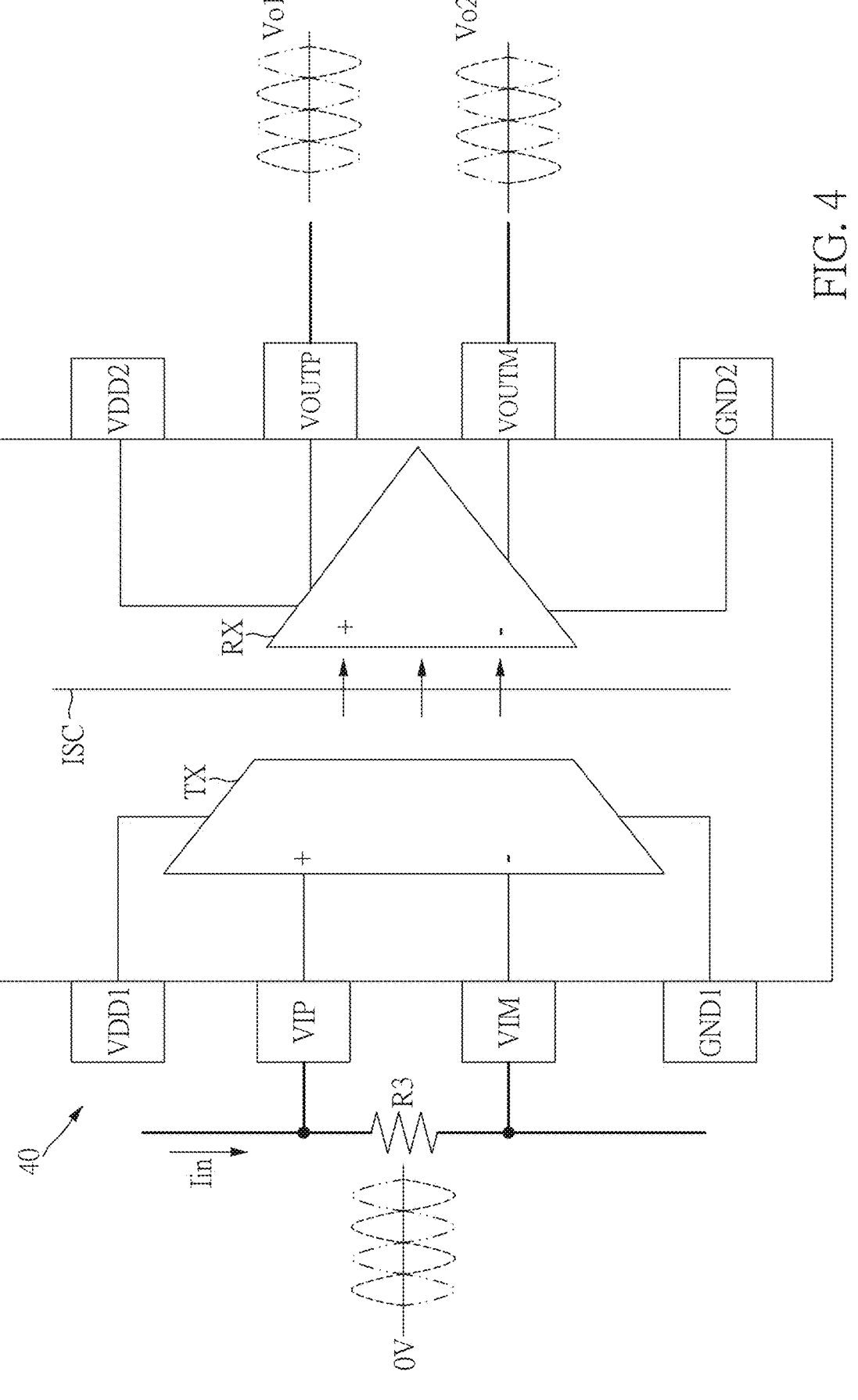
FIG. 4 is a schematic diagram of an optical isolation amplifier device according to the third embodiment of the present disclosure.

FIG. 4 is a schematic diagram of an optical isolation amplifier device according to a third embodiment of the present disclosure.

Referring to FIG. 4, an isolation amplifier device 40 implemented according to the block diagram of FIG. 3 is provided and includes a transmitting circuit TX, an isolation coupler ISC and a receiving circuit RX.

The transmitting circuit TX is connected to a first voltage node VDD1, differential input nodes VIP and VIM, and a first ground node GND1, and the isolation coupler ISC is coupled between the transmitting circuit TX and the receiving circuit RX.

In this case, the isolation coupler ISC is an optical isolation coupler, and can include a light-emitting diode (LED) and a light sensor which are connected to the transmitting circuit TX and the receiving circuit RX, respectively.

Moreover, the receiving circuit RX is connected to a second voltage node VDD2, differential input nodes VOUTP and VOUTM, and a second ground voltage node GND2. The receiving circuit RX can be configured to receive modulated light signals emitted from the LED, demodulates the light signals, and filters out high frequency components with low pass filters and amplifies the low frequency signals by using the offset voltage compensation circuit 300 and then output a differential pair of output voltages through the differential output nodes VOUTP and VOUTM.

In some embodiments, the isolation amplifier device 40 can be applied to a motor for sensing current and voltage variations. In this case, an alternating current Iin may flow through a resistor R3 of the motor that is driven and a voltage drops can be sensed by the isolation amplifier device 40. A differential pair of output voltages Vo1 and Vo2 that are proportional to the alternating current Iin can be created on an output side (i.e., the differential output nodes VOUTP and VOUTM) of the isolation coupler ISC.

Figure 5:
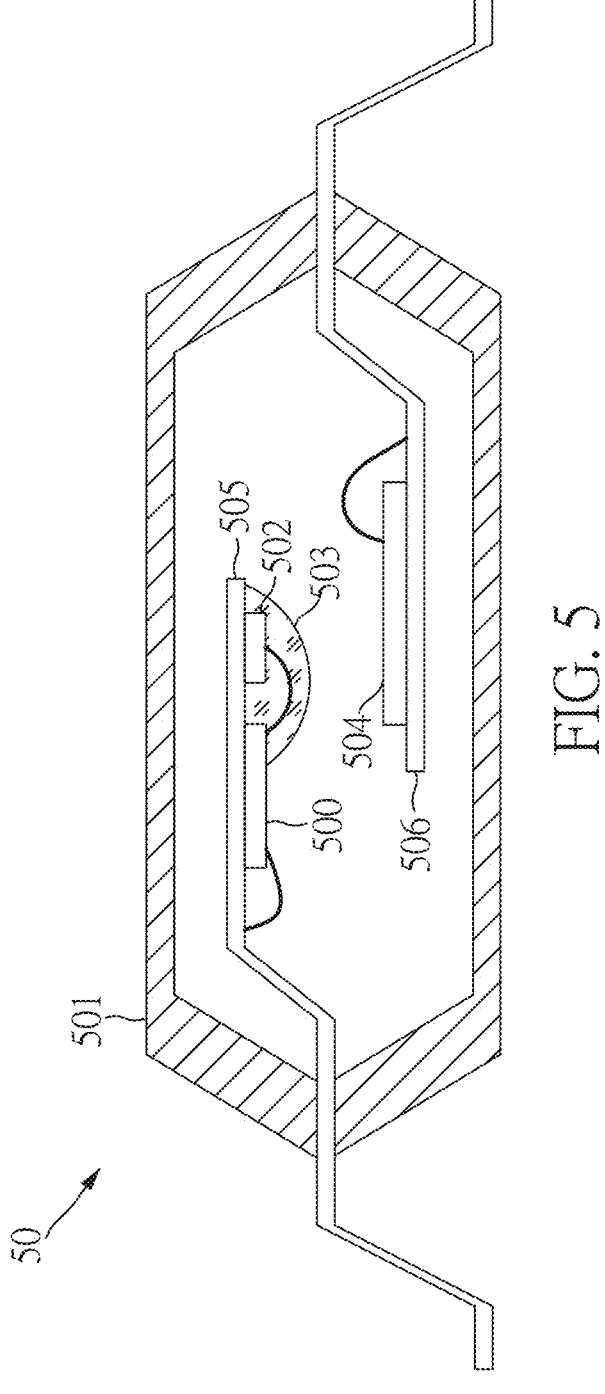
FIG. 5 is a schematic diagram of another optical isolation amplifier device according to the third embodiment of the present disclosure.

FIG. 5 is a schematic diagram of another optical isolation amplifier device according to the third embodiment of the present disclosure. Referring to FIG. 5, an isolation amplifier device 50 implemented according to the block diagram of FIG. 3 is provided and includes a transmitting chip 500, a housing 501, a light-emitting chip 502, an outer mold 503 and a receiving chip 504.

The housing 501 has an internal space for accommodating the transmitting chip 500, the light-emitting chip 502, the outer mold 503 and the receiving chip 504. The housing 501 can be made of opaque material such as epoxy for providing protection and resistant to optical interference for the light-emitting chip 502.

The transmitting chip 500, the light-emitting chip 502 and the outer mold 503 can be disposed on a first circuit board 505, and the receiving chip 504 can be disposed on a second circuit board 506. The first circuit board 505 has multiple circuit traces used to provide electrical connections for the transmitting chip 500 and the light-emitting chip 502. Similarly, the second circuit board 506 also has multiple circuit traces used to provide electrical connections for the receiving chip 504.

The outer mold 503 covers the light-emitting chip 502 and can be dome-shaped. The outer mold 503 can be made of a transparent material such as epoxy, so as to provide protection and optical enhancement for the light-emitting chip 502.

The transmitting chip 500 can be a 1-bit sigma-delta modulator (SDM) circuit, which is configured to convert a differential input voltage to a modulated pulse signal, the modulated pulse signal can be used to drive the light-emitting chip 502. The light-emitting chip 502 can be an infrared light-emitting diode, which emits lights after being driven by the transmitting chip 500, and the emitted lights serve as isolation signals.

The receiving chip 504 can receive the isolation signal, such as a light power of the light-emitting chip 502, and then demodulates the isolation signal, filters out high frequency components with a low pass filter, amplifies the low frequency signals and then output a differential analog voltage.

Beneficial Effects of the Embodiments

In conclusion, in the offset voltage compensation circuit and the isolation amplifier device including the same provided by the present disclosure, the compensation circuit arranged in the last output stage can compensate the output offset voltage, so as to achieve relaxation of accuracy requirement.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An offset voltage compensation circuit, comprising:
   a first amplifier having a first input connected to a first differential input node and a first output connected to a first differential output node;
   a second amplifier having a first input connected to a second differential input node and a second output connected to a second differential output node;
   a first current source connected to a second input of the first amplifier for providing a first current;
   a second current source connected to a second input of the second amplifier and configured for providing a second current;
   a first resistor connected to the second input of the first amplifier;
   a second resistor connected to the second input of the second amplifier;
   wherein the first current source is controlled according to the second current and a difference between a first initial output voltage and a second initial output voltage, such that an offset voltage between the first output and the second output is compensated.

2. The offset voltage compensation circuit according to claim 1, wherein the first amplifier is a first non-inverting amplifier, and the second amplifier is a second non-inverting amplifier; and
   wherein the first resistor is connected between the first output and the second input of the first amplifier, and the second resistor is connected between the second output and the second input of the second amplifier.

3. The offset voltage compensation circuit according to claim 2, further comprising:
   a first filter connected between the first differential input node and the first input of the first amplifier; and
   a second filter connected between the second differential input node and the first input of the second amplifier.

4. The offset voltage compensation circuit according to claim 2, wherein the first input and the second input of the first amplifier are a first positive input and a first negative input, respectively, and the first input and the second input of the second amplifier are a second positive input and a second negative input, respectively.

5. The offset voltage compensation circuit according to claim 3, wherein the first filter and the second filter are passive resistor-capacitor filters.

6. The offset voltage compensation circuit according to claim 1, wherein the first amplifier is a first inverting amplifier, and the second amplifier is a second inverting amplifier, wherein the first resistor is connected between a common-mode voltage node and the second input of the first amplifier, and the second resistor is connected between the common-mode voltage node and the second input of the second amplifier.

7. The offset voltage compensation circuit according to claim 6, further comprising:

a third filter connected between the first differential input node and the first input of the first amplifier;

a fourth filter connected between the second differential input node and the first input of the second amplifier;

a first resistor-capacitor network connected between the first output and the first input of the first amplifier; and a second resistor-capacitor network connected between the second output and the first input of the second amplifier.

8. The offset voltage compensation circuit according to claim 6, wherein the first input and the second input of the first amplifier are a first negative input and a first positive input, respectively, and the first input and the second input of the second amplifier are a second negative input and a second positive input, respectively.

9. The offset voltage compensation circuit according to claim 7, wherein the third filter and the fourth filter are passive resistor-capacitor filters.

10. The offset voltage compensation circuit according to claim 1, wherein resistances of the first resistor and the second resistor are equal, and the first current is controlled to a current value that is inversely proportional to the resistance of the first resistor or the second resistor.

11. The offset voltage compensation circuit according to claim 1, wherein the first amplifier and a second amplifier have a predetermined gain, and the first current source is further controlled according to the predetermined gain, the second current and the difference between the first initial output voltage and the second initial output voltage, such that the offset voltage between the first output and the second output is compensated.

12. An isolation amplifier device, comprising:

a transmitting circuit configured to convert a differential input voltage to a modulated pulse signal;

an isolation coupler configured to be driven by the modulated pulse signal and generate an isolation signal; and a receiving circuit configured to receive, demodulate, and amplify the isolation signal, so as to generate a differential output voltage, wherein the receiving circuit includes an output stage for amplifying the isolation signal, and the output stage has an offset voltage compensation circuit, which includes:

a first amplifier having a first input connected to a first differential input node and a first output connected to a first differential output node;

a second amplifier having a first input connected to a second differential input node and a second output connected to a second differential output node;

a first current source connected to a second input of the first amplifier for providing a first current;

a second current source connected to a second input of the second amplifier and configured to provide a second current;

a first resistor connected between the second input of the first amplifier and the first output; and a second resistor connected between the second input of the second amplifier and the second output;

wherein the first current source is controlled according to the second current and a difference between a first initial output voltage and a second initial output voltage, such that an offset voltage between the first output and the second output is compensated.

13. The isolation amplifier device according to claim 12, further comprising:

a first filter connected between the first differential input node and the first input of the first amplifier; and a second filter connected between the second differential input node and the first input of the second amplifier.

14. The isolation amplifier device according to claim 13, wherein the first amplifier is a first non-inverting amplifier, and the second amplifier is a second non-inverting amplifier; and wherein the first resistor is connected between the first output and the second input of the first amplifier, and the second resistor is connected between the second output and the second input of the second amplifier.

15. The isolation amplifier device according to claim 14, wherein the first input and the second input of the first amplifier are a first positive input and a first negative input, respectively, and the first input and the second input of the second amplifier are a second positive input and a second negative input, respectively.

16. The isolation amplifier device according to claim 13, wherein the first amplifier is a first inverting amplifier, and the second amplifier is a second inverting amplifier, wherein the first resistor is connected between a common-mode voltage node and the second input of the first amplifier, and the second resistor is connected between the common-mode voltage node and the second input of the second amplifier.

17. The isolation amplifier device according to claim 16, further comprising:

a first resistor-capacitor network connected between the first output and the first input of the first amplifier; and a second resistor-capacitor network connected between the second output and the first input of the second amplifier.

18. The isolation amplifier device according to claim 16, wherein the first input and the second input of the first amplifier are a first negative input and a first positive input, respectively, and the first input and the second input of the second amplifier are a second negative input and a second positive input, respectively.

19. The isolation amplifier device according to claim 12, wherein resistances of the first resistor and the second resistor are equal, and the first current is controlled to a current value that is inversely proportional to the resistance of the first resistor or the second resistor.

20. The offset voltage compensation circuit according to claim 12, wherein the first amplifier and the second amplifier have a predetermined gain, and the first current source is further controlled according to the predetermined gain, the second current and the difference between the first initial output voltage and the second initial output voltage, such that the offset voltage between the first output and the second output is compensated.

* * * * *